(12) United States Patent
Breyne et al.

(10) Patent No.: US 6,506,538 B1
(45) Date of Patent: Jan. 14, 2003

(54) NAPHTHOPYRANS ANNELATED IN $C_5$–$C_6$, THEIR PREPARATION AND COMPOSITIONS AND (CO)POLYMER MATRICES CONTAINING THEM

(75) Inventors: Olivier Breyne; You-Ping Chan; Patrick Jean, all of Lyons (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/393,213

(22) Filed: Sep. 9, 1999

(30) Foreign Application Priority Data

Sep. 11, 1998 (FR) .............................. 98 11519
Jan. 6, 1999 (FR) .............................. 99 00162

(51) Int. Cl.⁷ .......................................... C07D 311/94
(52) U.S. Cl. .................. 430/270.17; 430/19; 549/381; 549/382; 252/586; 524/110
(58) Field of Search ............... 430/19, 321, 270.17, 430/945; 549/381, 382; 524/110; 252/586

(56) References Cited

U.S. PATENT DOCUMENTS

| | | | | |
|---|---|---|---|---|
| 5,066,818 A | * | 11/1991 | Gemert et al. | 549/389 |
| 5,384,077 A | * | 1/1995 | Knowles | 549/389 |
| 5,514,817 A | | 5/1996 | Knowles | 549/384 |
| 5,565,147 A | | 10/1996 | Knowles et al. | 549/384 |
| 5,645,767 A | | 7/1997 | Van Gemert | 549/382 |
| 5,783,116 A | | 7/1998 | Lin | 549/384 |
| 5,869,658 A | | 2/1999 | Lin et al. | 549/382 |
| 5,955,520 A | | 9/1999 | Heller et al. | 549/382 |
| 5,961,892 A | | 10/1999 | Gemert et al. | 549/382 |
| 6,022,495 A | | 2/2000 | Kumar | 549/382 |
| 6,022,497 A | | 2/2000 | Kumar | 252/586 |
| 6,096,246 A | * | 8/2000 | Chan et al. | 549/389 |
| 6,146,554 A | * | 11/2000 | Melzig et al. | 549/382 |

FOREIGN PATENT DOCUMENTS

| | | | |
|---|---|---|---|
| WO | WO 96 14596 | | 5/1996 |
| WO | WO 97/48762 | | 12/1997 |
| WO | WO 99/15518 | | 4/1999 |
| WO | WO 01/19813 | * | 3/2001 |

* cited by examiner

*Primary Examiner*—Martin Angebranndt
(74) *Attorney, Agent, or Firm*—Angela N. Nwaneri; Peter Rogalskyj

(57) ABSTRACT

The present invention relates to novel compounds of the naphthopyran type which have an annelated carbocycle in position 5,6. These compounds are of formula (I) given below:

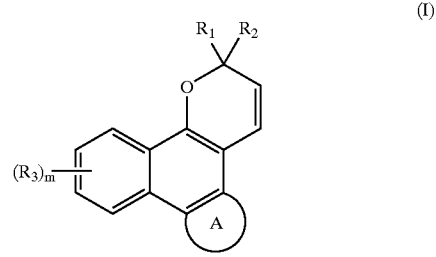

in which A is an alicyclic ring which is optionally annelated with an aromatic ring and in which two adjacent $R_3$ can together form at least one ring, for example a benzo group. These compounds (I) possess interesting photochromic properties. The invention also relates to the method of preparing these compounds (I), as well as their applications as photochromes and compositions and (co)polymer matrices comprising them.

15 Claims, No Drawings

NAPHTHOPYRANS ANNELATED IN $C_5$–$C_6$, THEIR PREPARATION AND COMPOSITIONS AND (CO)POLYMER MATRICES CONTAINING THEM

The present invention relates to novel annelated naphthopyran-type compounds which have, in particular, photochromic properties. The invention also relates to photochromic compositions and photochromic ophthalmic articles (lenses for example) which contain said naphthopyrans. The invention also covers the preparation of these novel naphthopyrans.

The photochromic compounds are capable of changing colour under the influence of a poly- or monochromatic light (UV for example) and of returning to their initial colour when the luminous irradiation ceases, or under the influence of temperature and/or a poly- or monochromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:
- a high transmission in the absence of ultraviolets,
- a low transmission (high colourability) under solar irradiation,
- adapted coloration and discoloration kinetics,
- a tint acceptable to the consumer (grey or brown preferably) with preferably a maintenance of the chosen tint during the coloration and the discoloration of the lens,
- a maintenance of the performances, the properties, within a temperature range of 0–40° C.,
- a significant durability, since these objectives sought after are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a grey or brown tint may necessitate the use of at least two photochromes of different colours, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic or inorganic support.

Amongst the numerous photochromic compounds described in the prior art, benzopyrans or naphthopyrans may be cited which are described in patents or patent applications: U.S. Pat. Nos. 3,567,605, 3,627,690, 4,826,977, 5,200,116, 5,238,981, 5,411,679, 5,429,744, 5,451,344, 5,458,814, 5,651,923, 5,645,767, 5,698,141, WO-A-95 05382, FR-A-2,718,447, WO-A-96 14596, and WO-A-97 21698 which are of the reduced formula below:

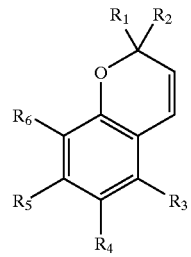

The U.S. Pat. No. 5,645,767 describes naphthopyrans which have an indeno group linked to carbons 5 and 6 of the naphtho skeleton:

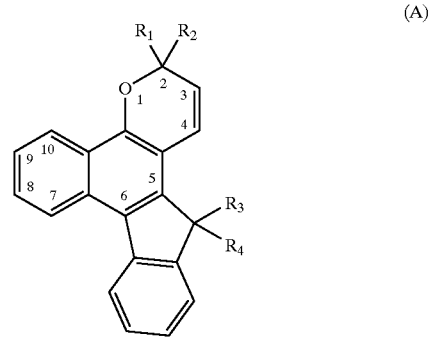

(A)

The U.S. Pat. No. 5,651,923 describes naphthopyrans having a naphthofurano or benzo group linked to carbons 5 and 6 of the naphtho skeleton.

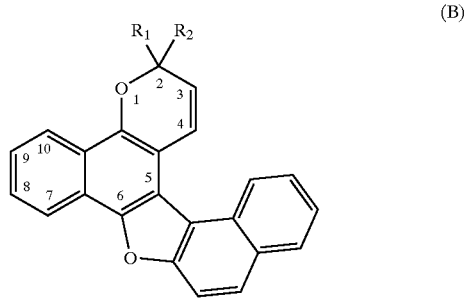

(B)

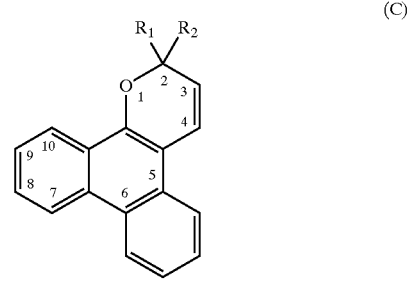

(C)

The U.S. Pat. No. 5,783,116 describes naphthopyrans having a non-substituted alicyclic group.

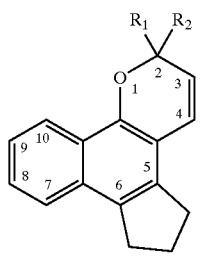

(D)

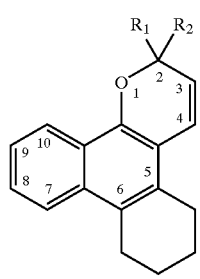

(E)

These known compounds A, B, C, D, E claim to satisfy the specifications defined supra. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

The photochromic compounds according to U.S Pat. No. 5,645,767 are obtained from substituted or non-substituted benzophenones, which are allowed to react with a succinic acid ester, such as the dimethyl ester, in the presence of toluene and potassium tert-butoxide. A half-ester is thus produced which is successively converted into acetoxynaphthalene and then into carboxynaphthol which is cyclised to obtain a naphthol fused with a benzofuranone residue. The reaction of this latter compound with a propargylic alcohol in the presence of DBSA leads to a naphthopyran fused with an indenone ring. The indene homologue of this naphthopyran can be obtained by starting from a precursor having a reduced ketone function. This carbon of the indene can be substituted in various ways.

As for the naphthopyrans fused with benzo or naphthofuran residues according to U.S. Pat. No. 5,657,923, they are prepared by reaction of a naphthol fused with an indenone ring or a naphthofuran ring, on the one hand, and with a propargylic alcohol on the other. The naphthol fused with an indenone ring is obtained for example as described in U.S. Pat. No. 5,645,767; while the naphthol fused with a naphthofuran ring originates from a reaction between a naphthoquinone and a 1,3-dihydroxynaphthalene, with or without subsequent methylation of at least one hydroxy.

In this context, it is to the credit of the inventors for having been interested in the above-mentioned naphthopyrans and for having selected, within this family of naphthopyrans fused in $C_5$–$C_6$ with at least one carbocycle, a group of specific molecules having particularly advantageous photochromic properties.

The present invention thus relates, according to a first of its aspects, to the compounds of formula (I):

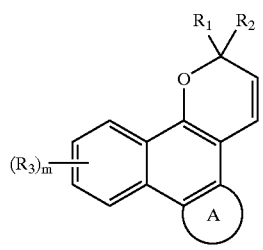

(I)

in which:
$R_1$ and $R_2$ are identical or different and independently represent:
hydrogen,
a linear or branched alkyl group which comprises 1 to 12 carbon atoms,
a cycloalkyl group which comprises 3 to 12 carbon atoms,
an aryl or heteroaryl group which comprises in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:
a halogen, and notably fluorine, chlorine and bromine,
a hydroxy group,
a linear or branched alkyl group which comprises 1 to 12 carbon atoms,
a linear or branched alkoxy group which comprises 1 to 12 carbon atoms,
a haloalkyl or haloalkoxy group corresponding respectively to the ($C_1$–$C_{12}$) alkyl or alkoxy groups above which are substituted with at least one halogen atom, and notably a fluoroalkyl group of this type,
a phenoxy or naphthoxy group optionally substituted by at least one linear or branched alkyl or alkoxy group which comprises 1 to 6 carbon atoms,
a linear or branched alkenyl group which comprises 2 to 12 carbon atoms and notably a vinyl group or an allyl group,
an —$NH_2$ group,
an —NHR group, R representing a linear or branched alkyl group which comprises 1 to 6 carbon atoms,
a:

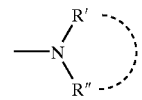

group,
R' and R", which are identical or different, independently representing a linear or branched alkyl group which comprises 1 to 6 carbon atoms, a phenyl group optionally substituted by at least one linear or branched alkyl or alkoxy group which comprises 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R'" group, which is a linear or branched alkyl group comprising 1 to 6 carbon atoms,
a methacryloyl group or an acryloyl group,
an aralkyl or heteroaralkyl group, the alkyl group, which is linear or branched, comprising 1 to 4 carbon atoms, and the aryl and heteroaryl groups having the definitions given above, or said two substituents $R_1$ and $R_2$ together form an adamantyl, norbornyl, fluorenylidene, di($C_1$–$C_6$)alkylanthracenylidene or spiro($C_5$–$C_6$)cycloalkylanthracenylidene group; said group being optionally substituted with at least one of the substituents listed above for $R_1$, $R_2$ corresponding to an aryl or heteroaryl group;

$R_3$, which are identical or different, represent, independently
 a halogen, and notably fluorine, chlorine or bromine,
 a linear or branched alkyl group which comprises 1 to 12 carbon atoms (advantageously 1 to 6 carbon atoms),
 a cycloalkyl group which comprises 3 to 12 carbon atoms,
 a linear or branched alkoxy group which comprises 1 to 12 carbon atoms (advantageously 1 to 6 carbon atoms),
 a haloalkyl, halocycloalkyl, haloalkoxy group corresponding respectively to the alkyl, cycloalkyl, alkoxy groups above, which are substituted with at least one halogen atom, notably selected from fluorine, chlorine and bromine,
 an aryl or heteroaryl group having the same definition as that given supra for $R_1$, $R_2$,
 an aralkyl or heteroaralkyl group, the alkyl group, which is linear or branched, comprising 1 to 4 carbon atoms and the aryl and heteroaryl groups having the same definitions as those given supra for $R_1$, $R_2$,
 a phenoxy or naphthoxy group optionally substituted by at least one linear or branched alkyl or alkoxy group which comprises 1 to 6 carbon atoms,
 an amine or amide group: —NH$_2$, —NHR, —CONH$_2$, —CONHR,

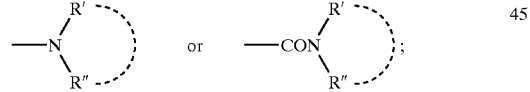

R, R', R" having their respective definitions given supra for the amine substituents of the values $R_1$, $R_2$: aryl or heteroaryl,
 an —OCOR$_8$ or —COOR$_8$ group, R$_8$ representing a straight or branched alkyl group comprising 1 to 6 carbon atoms or a cycloalkyl group comprising 3 to 6 carbon atoms or a phenyl group which is optionally substituted with at least one of the substituents listed above for the values of $R_1$, $R_2$: aryl or heteroaryl; or at least two adjacent $R_3$ groups together form at least one aromatic or non-aromatic cyclic group having a single ring or two annelated rings, optionally comprising at least one heteroatom selected from the group comprising: oxygen, sulphur and nitrogen, this or these annelated rings being optionally substituted with at least one substituent selected from those having the definition given above for the aryl or heteroaryl groups which can form $R_1$ and/or $R_2$;

m is an integer of 0 to 4;

A represents:

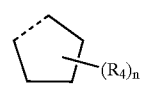 (A$_1$)

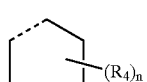 (A$_2$)

 (A$_3$)

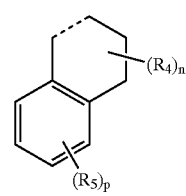 (A$_4$)

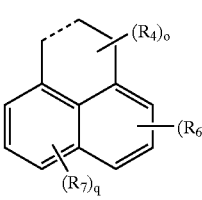 (A$_5$)

in these annelated rings (A$_1$) to (A$_5$):

the dashed line represents the carbon $C_5$ carbon $C_6$ bond of the naphthopyran ring of formula (I);

the α bond of the annelated ring (A$_4$) or (A$_5$) can be linked indifferently to carbon $C_5$ or to carbon $C_6$ of the naphthopyran ring of formula (I);

R$_4$, which are identical or different, represent, independently, an OH, an alkyl or alkoxy group which is linear or branched and which comprises 1 to 6 carbon atoms or two of the R$_4$ form a carbonyl (CO);

R$_5$, R$_6$ and R$_7$ represent, independently:
 a halogen, and notably fluorine, chlorine and bromine,
 a linear or branched alkyl group which comprises 1 to 12 carbon atoms (advantageously 1 to 6 carbon atoms),
 a haloalkyl group corresponding to the linear or branched above alkyl group, which is substituted with at least one halogen atom, notably a fluoroalkyl group,
 a cycloalkyl group which comprises 3 to 12 carbon atoms,
 a linear or branched alkoxy group which comprises 1 to 6 carbon atoms,
 a phenyl or benzyl group, optionally substituted with at least one of the substituents listed above in the definitions of the radicals $R_1$, $R_2$ of formula (I) in the case in which the radicals independently correspond to an aryl or heteroaryl group, a —NH$_2$, —NHR,

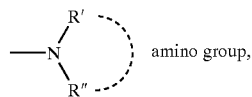 amino group,

R, R', R" having their respective definitions given supra for the amine substituents of the values R$_1$, R$_2$: aryl or heteroaryl, a phenoxy or naphthoxy group optionally substituted by at least one linear or branched alkyl or alkoxy group which comprises 1 to 6 carbon atoms, a —COR$_9$, —COOR$_9$ or —CONHR$_9$ group, R$_9$ representing a linear or branched alkyl group comprising 1 to 6 carbon atoms or a cycloalkyl group comprising 3 to 6 carbon atoms or a phenyl or benzyl group which is optionally substituted with at least one of the substituents listed above in the definitions of the radicals R$_1$, R$_2$ of formula (I) in the case in which the radicals independently correspond to an aryl or heteroaryl group, it being possible for two adjacent R$_5$ groups to together form a 5- to 6-membered aromatic or non-aromatic ring which can comprise at least one heteroatom selected from the group comprising: oxygen, sulphur and nitrogen;

n is an integer of 0 to 6, o is an integer of 0 to 2, p is an integer of 0 to 4 and q is an integer of 0 to 3;

with the condition according to which in (A$_1$) and (A$_2$) n is zero only in the case in which at least two of the adjacent R$_3$ substituents form at least one aromatic or non-aromatic cyclic group having a single ring or two annelated rings, optionally comprising at least one heteroatom selected from the group comprising: oxygen, sulphur and nitrogen, this or these annelated rings being optionally substituted with at least one substituent selected from those having the definition given above for the aryl groups which can form R$_1$ and/or R$_2$.

The compounds of the invention—naphthopyrans of formula (I)—possess a high colourability, even at 40° C., combined with discoloration kinetics which are adapted to the applications sought after. The colours, which are easily accessible, vary from orange to blue.

According to a first embodiment of the invention, the compounds considered are of formula (I) in which A corresponds to one of the annelated rings (A$_1$) or (A$_2$) as defined above.

According to a second embodiment of the invention, the compounds considered correspond to those of formula (I) in which A is one of the annelated rings (A$_3$), (A$_4$) or (A$_5$), as defined above.

It goes without saying that the invention also covers mixtures of compounds (I) which belong to at least two different types selected from the group comprising compounds (I) in which A=(A$_1$), those in which A=(A$_2$), those in which A=(A$_3$), those in which A=(A$_4$) and those in which A=(A$_5$).

According to a third embodiment of the invention, the compounds covered are those which belong to the family in which the compounds are of formula (I) with at least two of adjacent R$_3$ groups together forming an aromatic or non-aromatic cyclic group having a single ring (a phenyl group, for example) or two annelated rings (a benzofuran group, for example), optionally comprising at least one heteroatom selected from the group comprising: oxygen, sulphur and nitrogen, this or these annelated rings being optionally substituted with at least one substituent selected from those having the definition given above for the aryl or heteroaryl groups which can form R$_1$ and/or R$_2$.

The family according to this third embodiment comprises, inter alia, the compounds (I) in which two adjacent R$_3$ form at least one annelated ring, for example a benzo group, and in which carbons 5 and 6 of the phenanthrene skeleton are linked to at least one alicyclic and/or aromatic cycle A corresponding to (A$_1$), (A$_2$), (A$_3$), (A$_4$) or (A$_5$).

The compounds according to this third embodiment are, notably, naphthopyrans (I) in which two adjacent R$_3$ form at least one annelated ring, for example a benzo group, and in which carbons 5 and 6 of the phenanthropyran skeleton are linked to at least one substituted or non-substituted alicyclic or aromatic ring.

According to a fourth embodiment of the invention, the compounds envisaged are those of formula (I) given above, excluding the compounds in which A corresponds to (A$_1$) or (A$_2$) with at least one of the R$_4$ substituents different from hydrogen and in which at least two adjacent R$_3$ groups do not together form at least one aromatic or non-aromatic cyclic group having a single ring or two annelated rings, optionally comprising at least one heteroatom selected from the group comprising oxygen, sulphur and nitrogen, this or these annelated rings being optionally substituted with at least one substituent selected from those having the definition above for the aryl or heteroaryl groups which can form R$_1$ and/or R$_2$.

The compounds according to this fourth embodiment are, notably, naphthopyrans (I) in which two R$_3$ do not form an annelated ring, for example m=1 and R$_3$=—OMe, and in which carbons 5 and 6 of the naphtho skeleton are linked to at least one alicyclic ring A which is different from (A$_1$) and from (A$_2$).

Preferably, the compounds according to the invention are of formula (I) in which:

R$_1$, R$_2$ are identical or different and independently represent optionally substituted aryl or heteroaryl groups the basic structure of which is selected from those of phenyl, naphthyl, biphenyl, pyridyl, furyl, benzofuryl, dibenzofuryl, N—(C$_1$–C$_6$)alkylcarbazole, thienyl, benzothienyl, dibenzothienyl, julolidinyl groups; R$_1$ and/or R$_2$ advantageously representing a para-substituted phenyl group;

or R$_1$ and R$_2$ together form an adamantyl or norbornyl group.

The inventors also take the credit in that they have proposed, in this field of photochromes, a novel route of synthesis of the naphthopyrans fused with at least one carbocycle annelated on carbons 5 and 6, in which route a precursor of the naphthol type is obtained from at least one ketone which comprises at least one carbocycle and which is allowed to react with at least one alkyl cyanoacetate, the product obtained being then subjected to a cyclisation.

The invention also relates, according to a second of its aspects, to a method of preparation, notably of the compounds of formula (I) as defined above. This method essentially consists in carrying out the condensation:

of at least one compound having the formula (II) below:

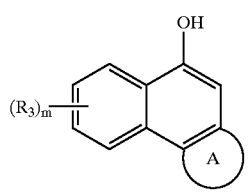
(II)

in which $R_3$, A and m are as defined supra with reference to the formula (I);

with at least one derivative of propargylic alcohol, having the formula (III) below:

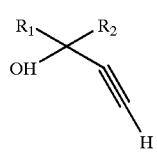
(III)

in which $R_1$ and $R_2$ are as defined supra with reference to the formula (I);

the (II)/(III) condensation being advantageously carried out in the presence of a catalyst, this catalyst being preferably selected from the group comprising para-toluenesulphonic acid, dodecylsulphonic acid and bromoacetic acid, or with at least one aldehyde derivative, having the formula (III') below:

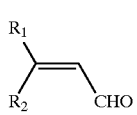
(III')

in which $R_1$ and $R_2$ are as defined supra with reference to the formula (I);

the (II)/(III') condensation being advantageously carried out in the presence of a metal complex, preferably a titanium complex, titanium (IV) ethoxide being particularly preferred.

In practice, the reaction of condensation between compounds (II) and (III) can be carried out in solvents such as toluene, xylene or tetrahydrofuran, optionally to which appropriate catalysts have been added.

As for the condensation of compounds (II) and (III'), reference may be made for more details to the patent application EP 0 562 915.

Said compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references). Aldehydes derived from (III), are obtained by rearrangement in an acid medium (cf. *J. Org. Chem.*, 1977, 42. 3403).

Said compounds of formula (II) are obtained according to a synthetic scheme the various steps of which are adaptations of known methods. The preferred general synthetic scheme is given below.

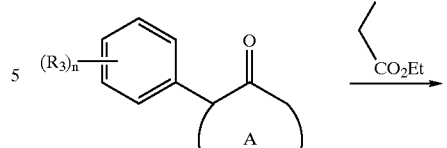

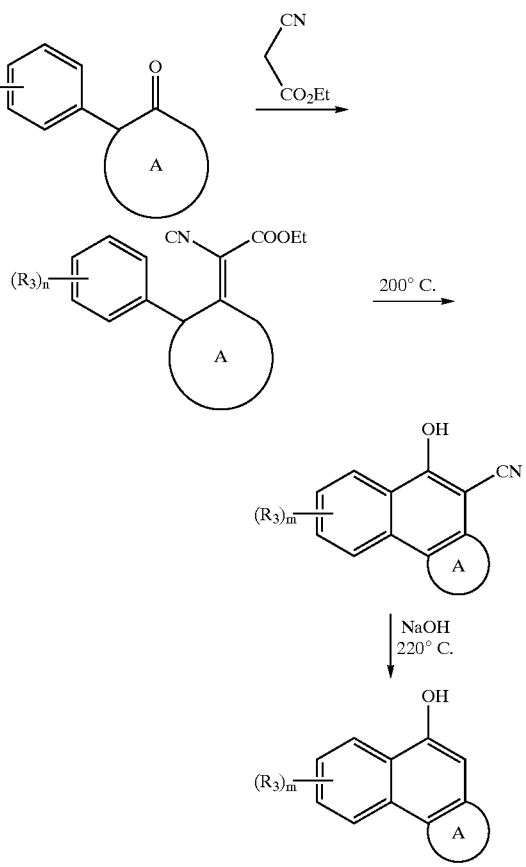

This synthetic route is inspired from the work of Sepiol et al. (*Synthesis* 1979, 290).

From where it ensues that the invention also covers a method of preparing the naphthol precursors of formula (II), characterised in that it comprises the following essential steps:

1—reaction of a precursor ($Ip_1$) of formula:

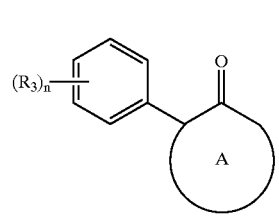
($Ip_1$)

with at least one alkyl cyanoacetate of formula $CN$—$CH_2$—$COOR^a$ with $R^a$=alkyl, preferably ethyl, so as to obtain the intermediate product ($IP_2$):

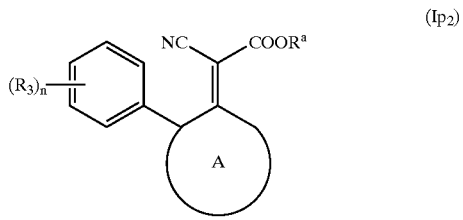
($Ip_2$)

2—thermal cyclisation of ($IP_2$) leading to the intermediate ($IP_3$):

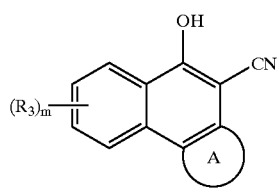

(Ip3)

3—high-temperature decyanation of (IP$_3$) to produce the intermediate (II).

The details on the whole of the method are given in the Examples which follow. In any case, it really is a matter of a novel synthetic route in the field of photochromes; and this route offers advantages in terms of ease of implementation and in economic terms.

According to a third of its aspects, the object of the invention is (co)polymer(s) and/or reticulate(s) obtained by polymerising and/or cross-linking at least one monomer comprising at least one compound (I) as defined above. Thus, the compounds (I) according to the invention can themselves be (co)monomers and/or can be comprised in (co)polymerisable and/or cross-linkable (co)polymers. The (co)polymers and/or reticulates thus obtained can constitute photochromic matrices such as those presented infra.

According to a fourth of its aspects, the present invention relates to the use of said compounds of formula (I) of the invention as photochromic agents. The object of the invention is, therefore:

firstly, novel photochromic compounds which are constituted by the naphthopyran derivatives such as defined above, taken alone or in a mixture of themselves and/or with at least one other photochromic compound of another type and/or with at least one non-photochromic colouring agent;

secondly, novel photochromic compositions which comprise at least one naphthopyran derivative (I) as defined above and/or one of its derivatives, and/or at least one linear or cross-linked (co)polymer containing at least one compound (I) according to the invention in its structure. Such photochromic compositions can contain at least one other photochromic compound, of another type and/or at least one non-photochromic colouring agent and/or at least one stabilising agent; these photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e.g. chromenes (U.S. Pat. Nos. 3,567,605, 5,238,981, WO-A-94 22850, EP-A-0 562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colouring agents which enable adjusting the tint, and/or one or more stabilising agents, such as an antioxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer subjected to UV. In general, a very low concentration of product (of the order of 0.01 to 5% by weight) is sufficient to obtain an intense coloration.

The compounds according to the invention are furthermore compatible with support matrices of organic polymer or of inorganic material, in a form included in said matrices as well as in the form of a coating of said matrices.

Also, within the context of the fourth aspect of the invention in relation to the photochromic applications, the object of the invention is a matrix which comprises:

at least one compound (I), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer, and/or copolymer and/or mixture of (co)polymers.

Following the example of their behaviour in solution, the compounds (I) included in a polymer matrix are colourless or slightly coloured in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable matrices, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The following products may be mentioned as examples of preferred polymer materials for forming matrices which are useful in optical applications of the photochromic compounds according to the invention:

alkyl, cycloalkyl, (poly or oligo)ethylene glycol, aryl or arylalkyl mono-, di-, tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, difunctional monomers having the formula below:

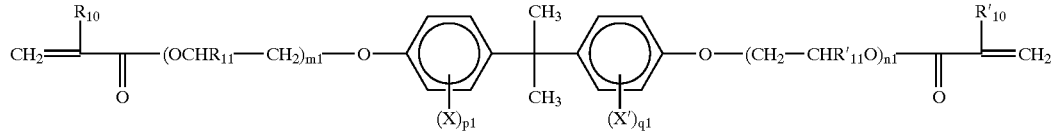

in which:

$R_{10}$, $R'_{10}$, $R_{11}$ and $R'_{11}$ are identical or different and represent independently a hydrogen or a methyl group;

$m_1$ and $n_1$ are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, and preferably those belonging to the group comprising: (meth)acrylic monomers, vinylic monomers, allylic monomers, and mixtures thereof.

In a particularly preferred manner, the photochromes of the invention are used with resins which have a nanobiphasic structure and which are obtained by copolymerising at least two different, specific difunctional monomers. Such resins have been described in the French application FR-A-2 762 845.

The amount of photochrome used in the (co)polymer matrix depends upon the degree of darkening desired. Usually, between 0.001 and 20% by weight of it is used.

Still according to the fourth of its aspects in relation to the applications of the naphthopyrans (I) as photochromes, another object of the present invention is ophthalmic articles, such as ophthalmic or solar spectacle articles, comprising:

at least one compound (I) according to the invention;

and/or at least one (co)polymer and/or reticulate formed, at least in part, from compound(s) of the invention;

and/or at least one photochromic composition as defined above;

and/or at least one matrix, (as defined supra), of an organic polymer material or of an inorganic material, or even of a hybrid inorganic-organic material, said matrix initially optionally comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . . .

The present invention is illustrated by the Examples which follow of synthesis and of photochromic validation, of compounds of the invention (naphthopyrans). Said compounds of the invention are compared to prior art compounds, $C_1$ and $C_2$.

EXAMPLES

Example 1

Synthesis of Compound (1)

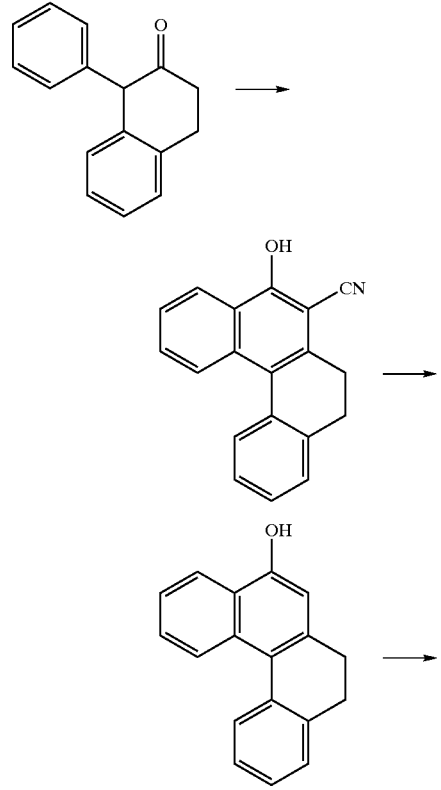

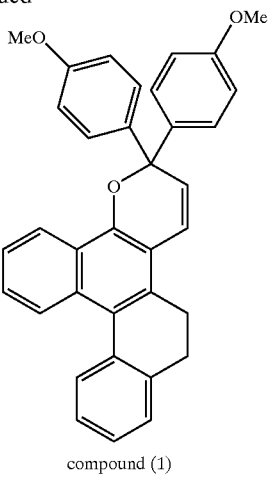

compound (1)

Step 1

The following mixture: 8.0 g of 1-phenyl-3,4-dihydro-1H-naphthalene-2-one (synthesised according to Mills et al., J. Chem. Soc. 1956, 4213), 3.9 ml of ethyl cyanoacetate, 7 g of ammonium acetate, 3.6 ml of acetic acid in 70 ml of toluene, is heated under reflux in a 100 ml conical flask equipped with a Dean Stark collector for 16 hours. The toluene is then distilled off and the mixture is left several hours at 220° C. (cyclisation of the intermediate of type $Ip_2$). The reaction mixture is then triturated in 50 ml of toluene and then filtered. 7.27 g of a yellow solid corresponding to the intermediate compound 2-cyano-1-naphthol (structure $Ip_3$) are obtained.

Step 2

The following mixture: 2.0 g of the product of the preceding step, 3 g of potassium hydroxide in 30 ml of n-butanol, is heated at about 200–220° C. in a 125 ml reactor for 6 hours. After cooling, the mixture is transferred into a flask and then reduced to dryness. The paste is then dissolved in 100 ml of water and then neutralised by the slow and progressive addition of concentrated hydrochloric acid (4 ml). The precipitate is recovered by filtration, washed with 4×20 ml of water and then dried under vacuum at 40° C. for one night. Yield 90%.

Step 3

The following mixture: 808 mg of the product of the preceding step, 1.05 g of 1,1-bis(para-methoxyphenyl)-propyn-1-ol is heated under reflux in the presence of a catalytic quantity of bromoacetic acid in 45 ml of xylene in a 100 ml reactor for 6 hours. The mixture is then evaporated to dryness and the product is then isolated by a chromatography on silica in eluting with toluene. The purest photochromic fractions are combined and are reduced to dryness. After a recrystallisation in THF/heptane, 640 mg of compound (1) are recovered in the form of a solid. Its structure is confirmed by NMR spectroscopy.

Example 2

Synthesis of Compound (2)

The following mixture: 701 mg of the product of step 2 of the preceding Example, 930 mg of 1-para-dimethylaminophenyl-1-phenyl-propyn-1-ol is heated under reflux in the presence of a catalytic quantity of bromoacetic acid in 25 ml of xylene in a 100 ml reactor for 6 hours. The mixture is then evaporated to dryness and the product is then isolated by a chromatography on silica in eluting with toluene. The purest photochromic fractions are combined and are reduced to dryness. 120 mg of compound (2) are obtained in the form of a solid. Its structure is confirmed by NMR spectroscopy.

Example 3

Synthesis of Compound (3)

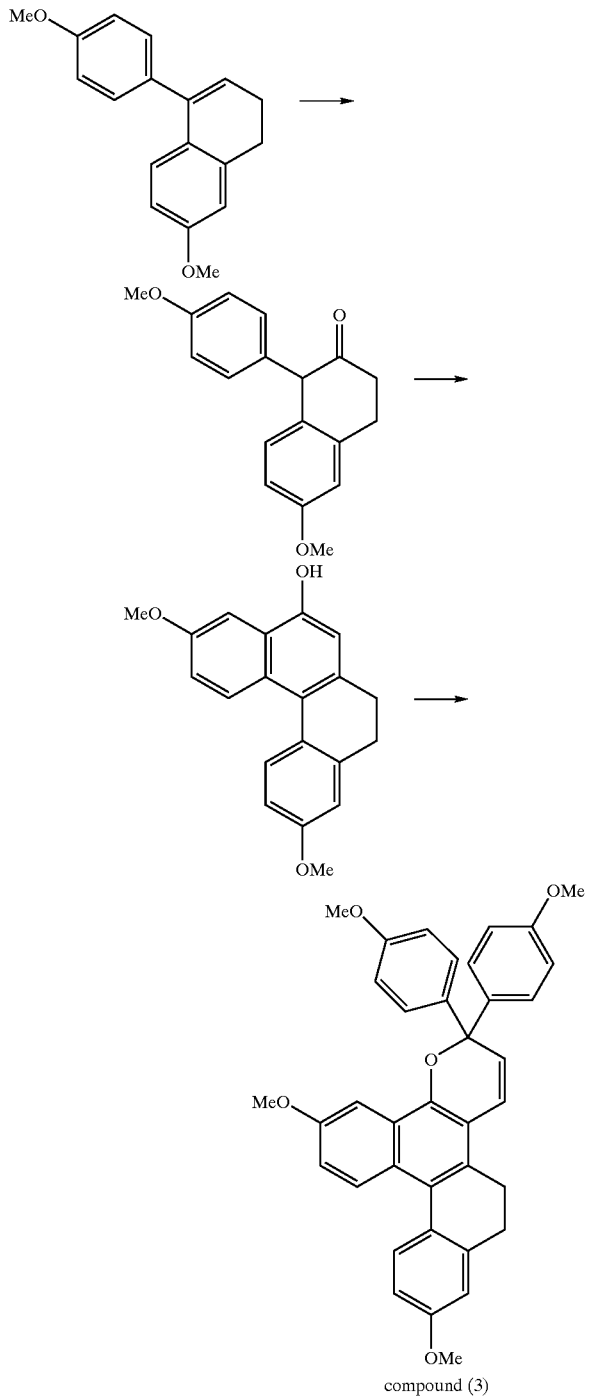

compound (3)

Step 1

The 1-(p-methoxyphenyl)-6-methoxy-3,4-dihydronaphthalene derivative (synthesised according to the method adapted from Org. Synth. Coll. Vol III, p 729) is converted into an epoxy derivative by rearrangement, in basic medium, of the corresponding bromohydrin (according to J. Org. Chem. 1986, 3407). The ketone is then obtained by rearrangement in an acidic medium of the epoxy derivative. The naphthol derivative of type II is then synthesised in the same way as before.

Step 2

Compound (3) is obtained by reaction of the derivative of the preceding step with the 1,1-bis(p-methoxyphenyl)-propyn-1-ol as in Example 1. The product (3) is obtained after purification. Its structure is confirmed by NMR spectroscopy.

Example 4

Synthesis of Compound (4)

Compound (4) is obtained by reaction of the derivative intermediate of type II of the preceding Example with the 1-paradimethylaminophenyl-1-p-methoxy-phenyl-propyn-1-ol as in Example 1. The product (4) is obtained after purification. Its structure is confirmed by NMR spectroscopy.

Example 5

Synthesis of Compound (5)

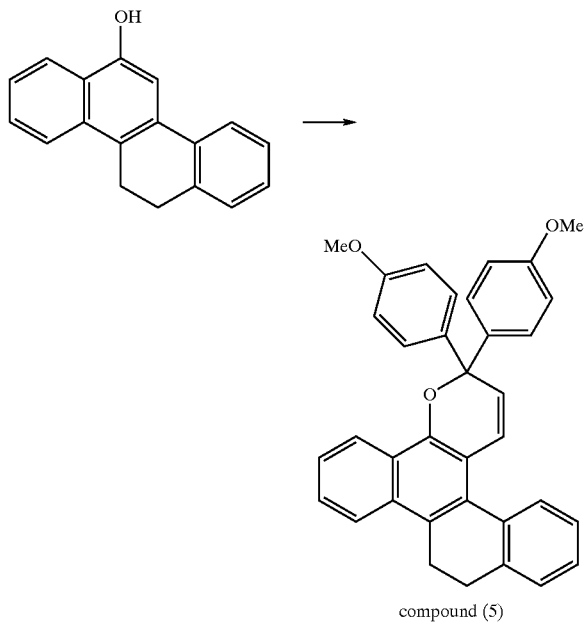

compound (5)

Compound (5) is obtained by reaction of the naphthol derivative (500 mg) above (obtained according to the method described by Newman et al., J. Amer. Chem. Soc. 1938, 60, 2947) with the 1,1-bis(p-methoxyphenyl)-propyn-1-ol (560 mg) as in Example 1 with a reflux time of 2 hours. 300 mg of compound (5) are obtained after purification. Its structure is confirmed by NMR spectroscopy.

Example 6

Synthesis of Compound (6)

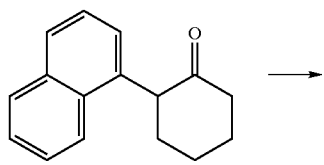

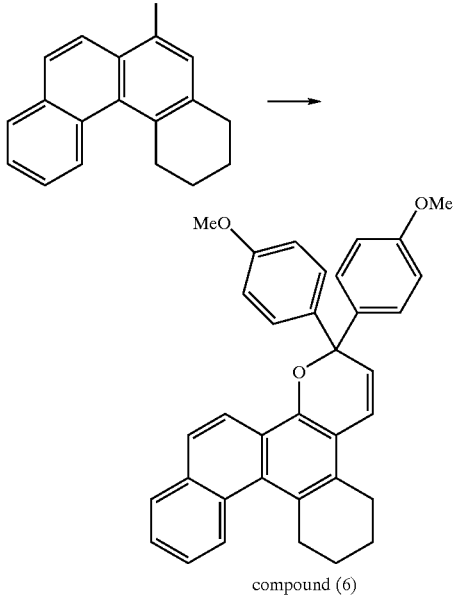

compound (6)

Step 1

The 2-(1-naphthyl)cyclohexanone derivative is prepared by reaction of the magnesium derivative of 1-bromonaphthalene with epoxycyclohexane (according to Takahashi et al., Tetrahedron Asym. 1995, 6, 617) followed by an oxidation with pyridinium chlorochromate (according to Corey et al. Tetrahedron Lett. 1975, 2647). The following mixture: 8.4 g of 2-(1-naphthyl)cyclohexanone, 4.3 g of ethyl cyanoacetate, 4 g of ammonium acetate, 4 ml of acetic acid in 40 ml of toluene, is heated under reflux in a 100 ml flask equipped with a Dean Stark collector, for 8 hours. The toluene is then distilled off and 15 g of acetamide are added. A temperature of 200° C. is then maintained for 3 hours. The hot medium is then poured into 200 ml of water and the solid precipitate is collected by filtration. A recrystallisation from ethanol enables obtaining 7.6 g of cyanated naphthol (Ip$_3$).

Step 2

The following mixture: 3.5 g of the product of the preceding step, 5 g of potassium hydroxide in 20 ml of n-butanol, is heated at about 200–230° C. in a 125 ml reactor, for 8 hours. After cooling, the mixture is transferred into a flask and then reduced to dryness. The paste is then dissolved in 100 ml of water and then neutralised by the slow and progressive addition of concentrated hydrochloric acid. The precipitate is recovered by filtration, washed with 4×20 ml of water and then dried under vacuum at 40° C. for one night. The naphthol (type II) is thus obtained in quantitative yield.

Step 3

The following mixture: 1 g of the product of the preceding step, 1.5 g of 1,1-bis(para-methoxyphenyl)-propyn-1-ol, is heated under reflux in the presence of a catalytic quantity of bromoacetic acid in 15 ml of xylene in a 100 ml reactor for 5 hours. The product is then purified by chromatography on silica in eluting with a toluene/heptane (70/30) mixture. The purest photochromic fractions are combined and are reduced to dryness. After recrystallisation from toluene/heptane, 230 mg of compound (6) are recovered. Its structure is confirmed by NMR spectroscopy.

Example 7
Synthesis of Compound (7)

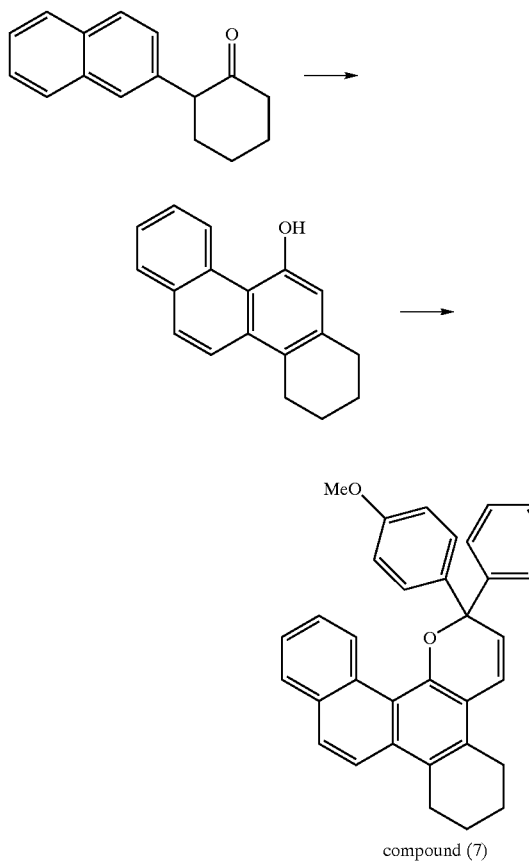

compound (7)

Compound (7) is synthesised in the same way as that described for compound (6). For the last step, 1 g of the naphthol is allowed to react with 1.1 g of 1,1-bis(para-methoxyphenyl)-propyn-1-ol in the presence of a catalytic quantity of bromoacetic acid in 20 ml of toluene. The product is then purified by chromatography on silica in eluting with a toluene/heptane (80/20) mixture. The purest photochromic fractions are combined and are reduced to dryness. After a recrystallisation from a toluene/diisopropyl ether mixture, 800 mg of compound (7) are recovered. Its structure is confirmed by NMR spectroscopy.

Example 8
Synthesis of Compound (8)

Compound (8) is obtained in a way analogous to that described for Example (6) in allowing the naphthol derivative to react with 1-(para-dimethylaminophenyl)-1-phenyl-propyn-1-ol.

Example 9
Synthesis of Compound (9)

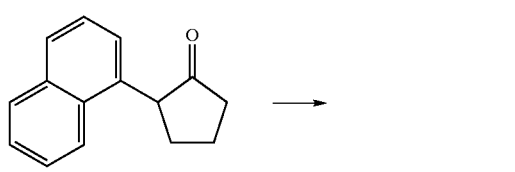

-continued

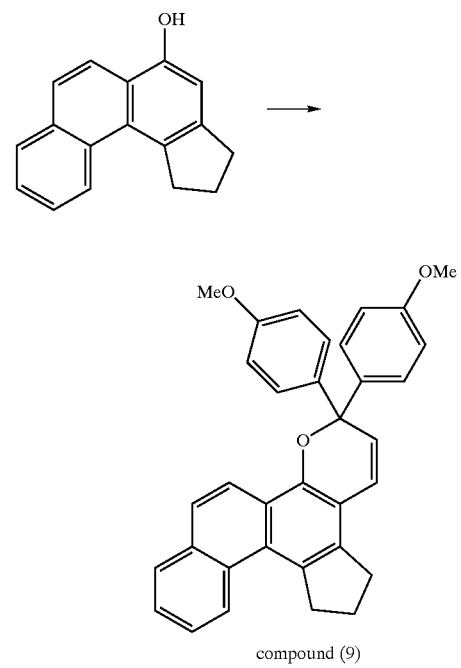

compound (9)

Compound (9) is obtained in a way analogous to that described for Example (6) in starting with 2-(1-naphthyl) cyclopentanone.

Example 10
Synthesis of Compound (10)

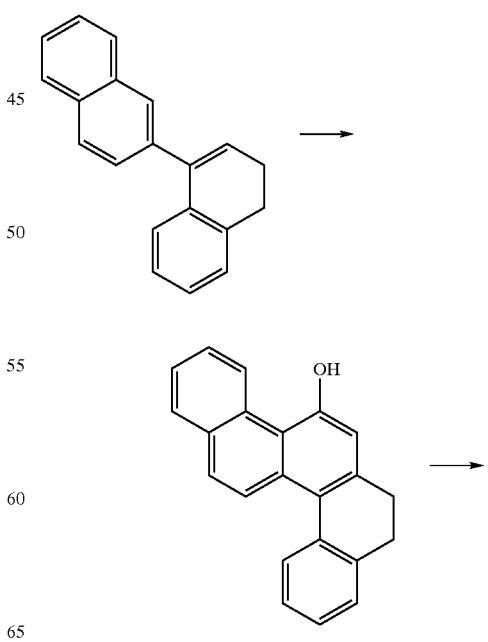

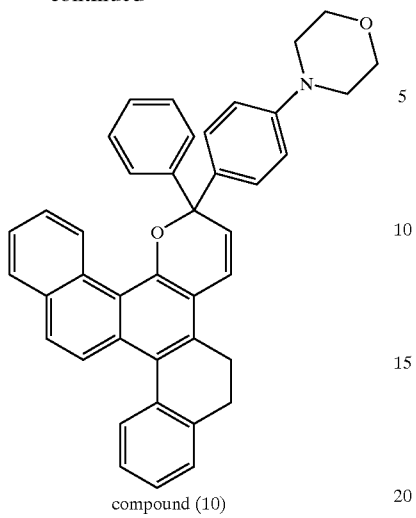

compound (10)

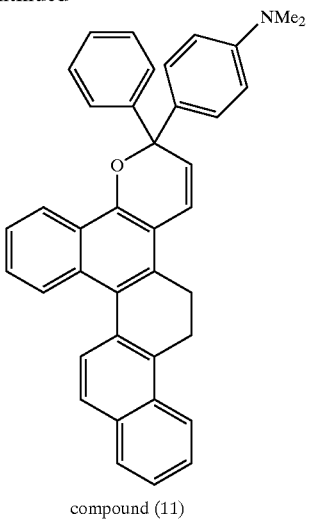

compound (11)

The intermediate phenanthrol was obtained according to the same method as that described in Example 3. Compound (10) is then obtained by coupling with 1-(para-morpholinophenyl)-1-phenyl-propyn-1-ol as described in Example 1. Its structure is confirmed by NMR spectroscopy.

The intermediate naphthol compound was obtained according to the same method as that indicated in Example 3, from the benzotetralone (obtained according to A. Eirin et al., Arch. Pharm. 1987, 320, 1110) instead of tetralone. Compound (11) is then obtained by coupling with 1-(para-dimethylaminophenyl)-1-phenyl-propyn-1-ol as described in Example 1, followed by a purification by chromatography. Its structure is confirmed by NMR spectroscopy.

Example 11

Synthesis of Compound (11)

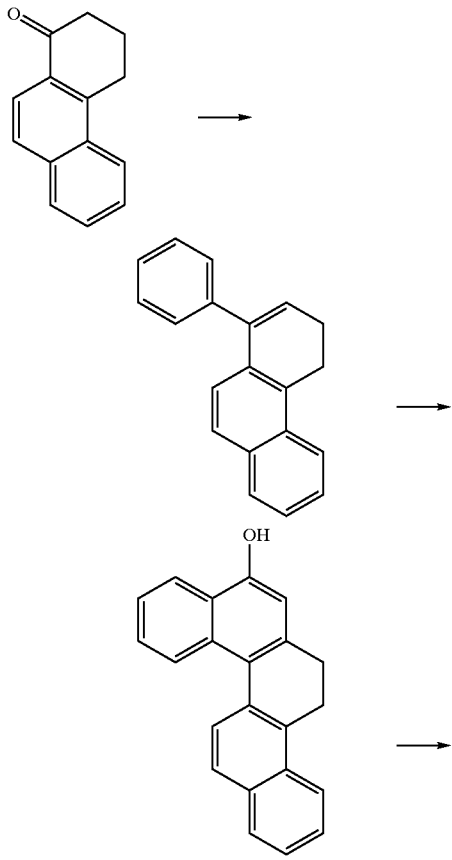

Example 12

Synthesis of Compound (12)

Compound 12 was obtained by reaction of the intermediate naphthol of Example 1 with 1-thienyl-1-phenyl-propyn-1-ol as described in the last step of Example 1, followed by a purification by chromatography. Its structure is confirmed by NMR.

Example 13

Synthesis of Compound (13)

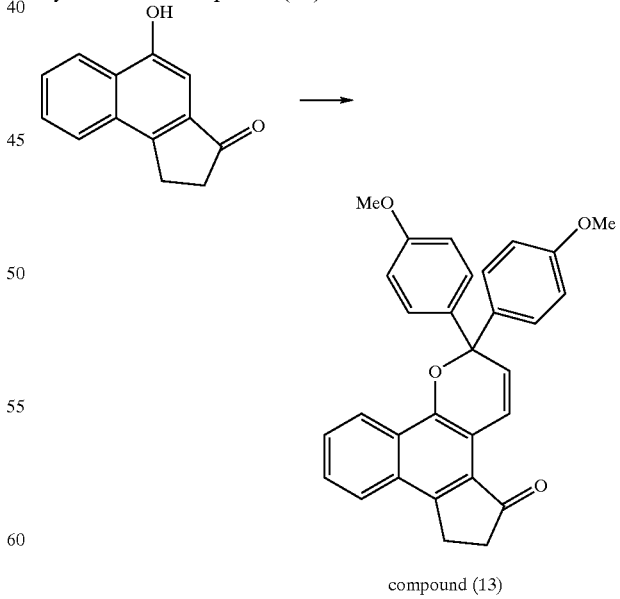

compound (13)

Compound 13 was obtained by reaction of the intermediate naphthol (obtained according to Robinson, *J. Chem. Soc.,* 1938, 1390) with 1,1-bis(para-methoxy-phenyl)-propyn-1-ol, followed by a purification by chromatography. Its structure is confirmed by NMR.

Example 14

Compounds C1, C2 and C3

Comparative compound C1 is synthesised from 1-naphthol and 1,1-bis(p-methoxyphenyl)-propyn-1-ol. It is of formula (C1). Compound C2 is of formula:

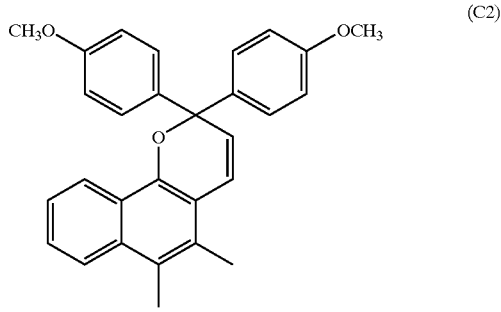
(C2)

Compound C2 is commercially available.

Compound C3 is described in the U.S. Pat. No. 5,783,116.

Example 15

The photochromic properties of said compounds (1) to (13), C1, C2 and C3 were evaluated.

Said compounds are dissolved, at the rate of 5 mg in 50 ml of THF and the UV-visible absorptions are then measured (optical path of 1 cm) before and after exposure to a UV source at 365 nm. The observation of the tints and the intensities developed is made by placing the solutions in the sun or before a solar simulator. The properties of these compounds are given in the Table below.

| COMPOUND | STRUCTURE | $\lambda_1$* | $\lambda_2$** | T 1/2 (discoloration) | TINT |
|---|---|---|---|---|---|
| (1) | MeO—[structure]—OMe | 381 nm | 536 nm | 16 s | pink |
| (2) | [structure]—NMe$_2$ | 381 nm | 572 nm | 9 s | violet |

-continued

| COMPOUND | STRUCTURE | λ1* | λ2** | T 1/2 (discoloration) | TINT |
|---|---|---|---|---|---|
| (3) | 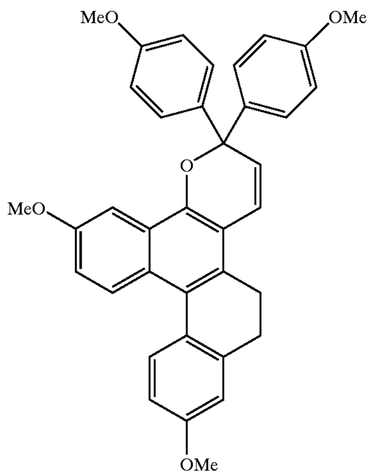 | 398 nm | 566 nm | 33 s | violet |
| (4) | 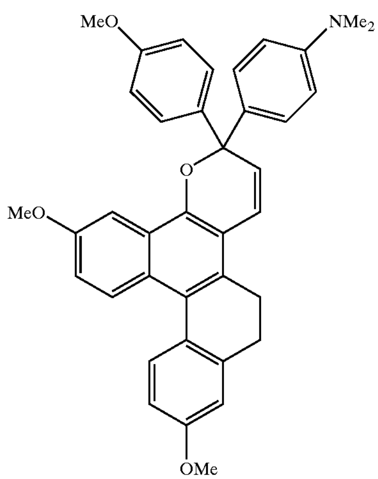 | 398 nm | 592 nm | 26 s | blue |
| (5) | 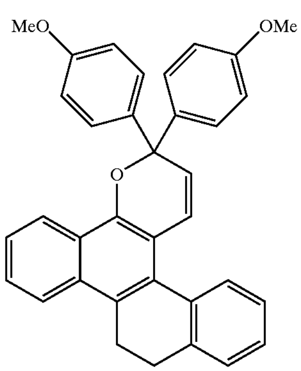 | 384 nm | 501 nm | 8 s | orange |

-continued

| COMPOUND | STRUCTURE | λ1* | λ2** | T 1/2 (discoloration) | TINT |
|---|---|---|---|---|---|
| (6) | 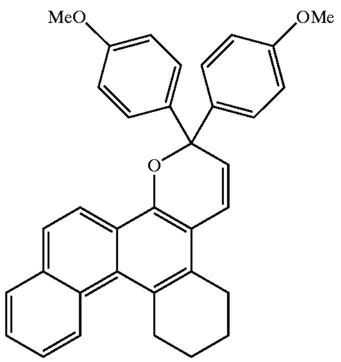 | 392 nm | 513 nm | 8 s | pink |
| (7) | 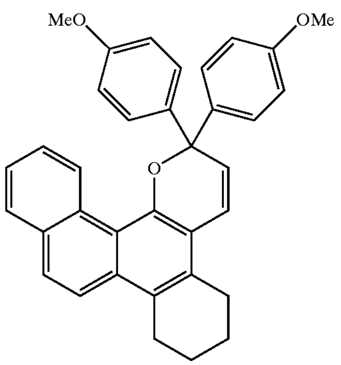 | 385 nm | 506 nm | 27 s | orange |
| (8) | 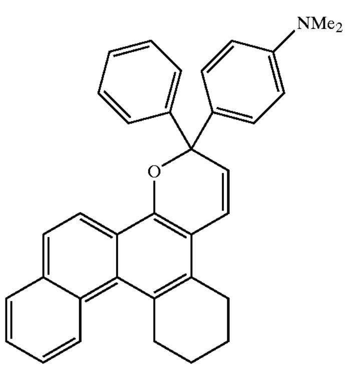 | 392 nm | 555 nm | 8 s | violet |
| (9) | 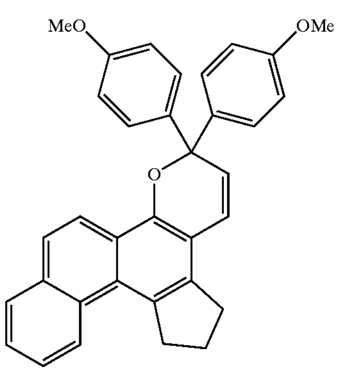 | 392 nm | 562 nm | 16 s | red brown |

-continued

| COMPOUND | STRUCTURE | λ1* | λ2** | T 1/2 (discoloration) | TINT |
|---|---|---|---|---|---|
| (10) | 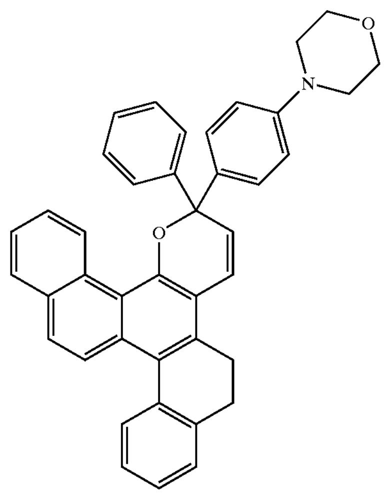 | 396 nm | 560 nm | 10 s | violet |
| (11) | 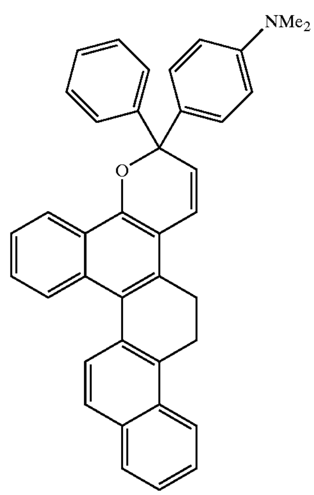 | 387 nm | 584 nm | 9 s | blue |
| (12) | 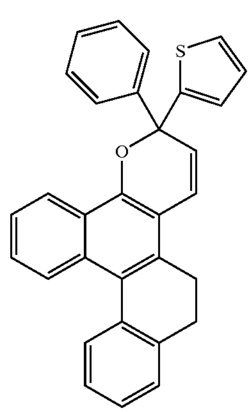 | 381 nm | 530 | 50 s | red |

-continued

| COMPOUND | STRUCTURE | λ1* | λ2** | T 1/2 (discoloration) | TINT |
|---|---|---|---|---|---|
| (13) | 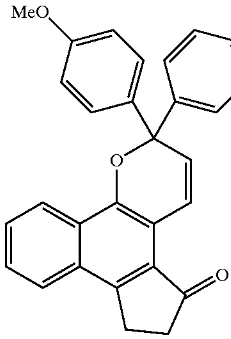 | 374 nm | 494 nm | 26 s | red |
| C1 | 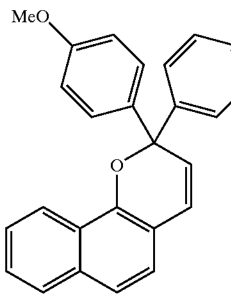 | 355 nm | 496 nm | >100 s | red |
| C2 | 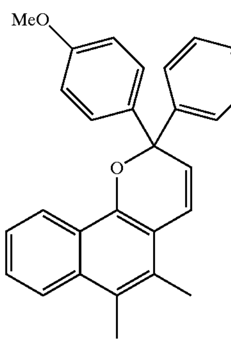 | 368 nm | 490 nm | 39 s | red |
| C3 | 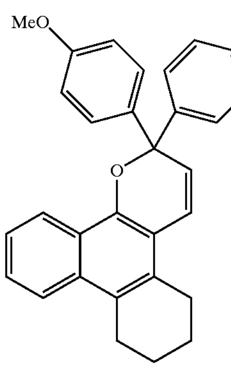 | 369 nm | 490 nm | 89 s | red |

*λ max of the band of the longest wavelength of the compound before exposure.
**λ max of the band of the longest wavelength of the compound after exposure.

The observation of the solutions in the presence of solar radiation or UV radiation shows that the compounds of the invention have λ1 and λ2 which are shifted towards longer wavelengths (bathochromic shift) and fast discoloration kinetics in comparison to analogous compounds C1, C2 and C3.

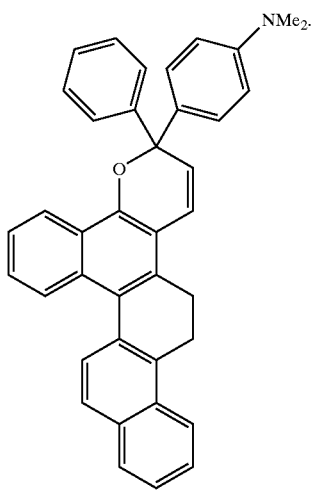
15. Compounds according to claim 1, characterised in that they have the following formula:
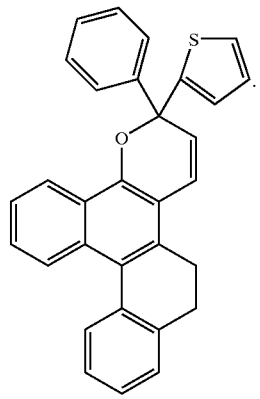

What is claimed is:

1. Compounds of the following formula (I):

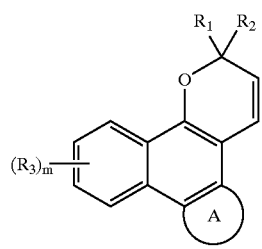

in which:

a $R_1$ and $R_2$ are identical or different and independently represent:
  hydrogen,
  a linear or branched alkyl group which comprises 1 to 12 carbon atoms,
  a cycloalkyl group which comprises 3 to 12 carbon atoms,
  an aryl or heteroaryl group which comprises in its basic structure 6 to 24 carbon atoms or 4 to 24 carbon atoms respectively and at least one heteroatom selected from sulphur, oxygen, and nitrogen; said basic structure being optionally substituted with at least one substituent selected from the group consisting of:
    a halogen,
    a hydroxy group,
    a linear or branched alkyl group which comprises 1 to 12 carbon atoms,
    a linear or branched alkoxy group which comprises 1 to 12 carbon atoms,
    a haloalkyl or haloalkoxy group corresponding respectively to the ($C_1$–$C_{12}$) alkyl or alkoxy groups above which are substituted with at least one halogen atom,
    a phenoxy or naphthoxy group optionally substituted by at least one linear or branched alkyl or alkoxy group which comprises 1 to 6 carbon atoms,
    a linear or branched alkenyl group which comprises 2 to 12 carbon atoms,
    an —$NH_2$ group,
    an —NHR group, R representing a linear or branched alkyl group which comprises 1 to 6 carbon atoms,
    a group having the formula:

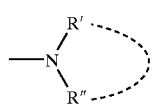

where R' and R", which are identical or different, independently representing a linear or branched alkyl group which comprises 1 to 6 carbon atoms, a phenyl group optionally substituted by at least one linear or branched alkyl or alkoxy group which comprises 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R''' group, which is a linear or branched alkyl group comprising 1 to 6 carbon atoms, and
    a methacryloyl group or an acryloyl group, or
  an aralkyl or heteroaralkyl group, the alkyl group, which is linear or branched, comprising 1 to 4 carbon atoms, and the aryl and heteroaryl groups having the definitions given above, or
said two said two substituents $R_1$ and $R_2$ together form an adamantyl, norbornyl, fluorenylidene, di($C_1$–$C_6$) alkylanthracenylidene, or spiro ($C_5$–$C_6$) cycloalkylanthracen-ylidene group; said group being optionally substituted with at least one of the substituents listed above for $R_1$, $R_2$ corresponding to an aryl or heteroaryl group;

$R_3$, which are identical or different, represent, independently:
  a halogen,
  a linear or branched alkyl group which comprises 1 to 12 carbon atoms,
  a cycloalkyl group which comprises 3 to 12 carbon atoms,
  a linear or branched alkoxy group which comprises 1 to 12 carbon atoms,
  a haloalkyl, halocycloalkyl, haloalkoxy group corresponding respectively to the alkyl, cycloalkyl, alkoxy groups above, which are substituted with at least one halogen atom,
  an aryl or heteroaryl group having the same definition as that given supra for $R_1$, $R_2$,
  an aralkyl or heteroaralkyl group, the alkyl group, which is linear or branched, comprising 1 to 4 carbon atoms and the aryl and heteroaryl groups having the same definitions as those given supra for $R_1$, $R_2$,
  a phenoxy or naphthoxy group optionally substituted by at least one linear or branched alkyl or alkoxy group which comprises 1 to 6 carbon atoms,
  an amine or amide group: —$NH_2$, —NHR, —$CONH_2$, —CONHR,

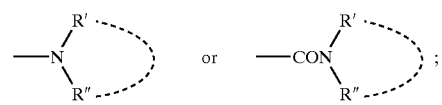

R, R', R" having their respective definitions given supra for the amine substituents of the values $R_1$, $R_2$: aryl or heteroaryl,
  an —$OCOR_8$ or —$COOR_8$ group, $R_8$ representing a straight or branched alkyl group comprising 1 to 6 carbon atoms or a cycloalkyl group comprising 3 to 6 carbon atoms or a phenyl group which is optionally substituted with at least one of the substituents listed above for the values of $R_1$, $R_2$: aryl or heteroaryl; or at least two adjacent $R_3$ groups together form at least one aromatic or non-aromatic cyclic group having a single king or two annelated rings, optionally comprising at least one heteroatom selected from the group comprising: oxygen, sulphur and nitrogen, this or these annelated rings being optionally substituted with at least one substituent selected from those having the definition given above for the aryl or heteroaryl groups which can form $R_1$ and/or $R_2$;

m is an integer of 0 to 4;

A represents:

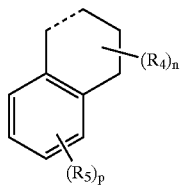

(A₄)

wherein, in this annelated ring ($A_4$)

the dashed line represents the carbon $C_5$ carbon $C_6$ bond of the naphthopyran ring of formula (I);

the α bond of the annelated ring ($A_4$) can be linked indifferently to carbon $C_5$ or to carbon $C_6$ of the naphthopyran ring of formula (I);

$R_4$, which are identical or different, represent, independently, an OH, an alkyl or alkoxy group which is linear or branched and which comprises 1 to 6 carbon atoms or two of the $R_4$ form a carbonyl (CO);

$R_5$ represents:
- a halogen,
- a linear or branched alkyl group which comprises 1 to 12 carbon atoms,
- a haloalkyl group corresponding to the linear or branched above alkyl group, which is substituted with at least one halogen atom;
- a cycloalkyl group which comprises 3 to 12 carbon atoms,
- a linear or branched alkoxy group which comprises 1 to 6 carbon atoms,
- a phenyl or benzyl group, optionally substituted with at least one of the substituents listed above in the definitions of the radicals $R_1$, $R_2$ of formula (I) in the case in which the radicals independently correspond to an aryl or heteroaryl group,
- a —$NH_2$, —NHR, or amino group having the formula:

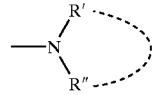

R, R', R" having their respective definitions given supra for the amine substituents of the values $R_1$, $R_2$: aryl or heteroaryl,

- a phenoxy or naphthoxy group optionally substituted by at least one linear or branched alkyl or alkoxy group which comprises 1 to 6 carbon atoms,
- a —$COR_9$, —$COOR_9$, or —CONHR, group, $R_9$ representing a linear or branched alkyl group comprising 1 to 6 carbon atoms or a cycloalkyl group comprising 3 to 6 carbon atoms or a phenyl or benzyl group which is optionally substituted with at least one of the substituents listed above in the definitions of the radicals $R_1$, $R_2$ of formula (I) in the case in which the radicals independently correspond to an aryl or heteroaryl group, and wherein two adjacent $R_5$ groups, taken together, optionally form a 5- to 6-membered aromatic or non-aromatic ring which can comprise at least one heteroatom selected from the group comprising: oxygen, sulphur, and nitrogen;

n is an integer of 0 to 4 and p is an integer of 0 to 4.

2. Compounds according to claim 1, of formula (I) in which at least two of the adjacent $R_3$ groups together form at least one aromatic or non-aromatic cyclic group having a single ring or two annelated rings, optionally comprising at least one heteroatom selected from the group consisting of oxygen, sulphur and nitrogen, this or these annelated rings being optionally substituted with at least one substituent selected from those having the definition given in claim 1 for the aryl or heteroaryl groups which can form $R_1$ and/or $R_2$.

3. Compounds according to claim 1, characterised in that they are of formula (I) in which:

$R_1$, $R_2$ are identical or different and independently represent optionally substituted aryl or heteroaryl groups, the basic structure of which is selected from those of phenyl, naphthyl, biphenyl, pyridyl, furyl, benzofuryl, dibenzofuryl, N—($C_1$–$C_6$)alkylcarbazole, thienyl, benzothienyl, dibenzothienyl, or julolidinyl groups; or $R_1$ and $R_2$ together form an adamantyl or norbornyl group.

4. A photochromic compound, characterised in that it is constituted by a compound according to claim 1, or by a mixture of at least two compounds according to claim 1, or by a mixture of at least one compound according to claim 1, with at least one other photochromic compound of another type and/or at least one non-photochromic colouring agent.

5. A photochromic composition, characterised in that it comprises:

at least one compound according to claim 1, and/or at least one linear or cross-linked (co)polymer which contains, in its structure, at least one compound (I) according to claim 1; and optionally, at least one other photochromic compound of another type and/or at least one non-photochromic colouring agent and/or at least one stabilising agent.

6. An ophthalmic or solar article comprising:

at least one compound according to claim 1.

7. The article according to claim 6, characterised in that it is constituted by a lens, by a glazing, or by an optical device.

8. Compounds according to claim 1, characterised in that they have the following formula:

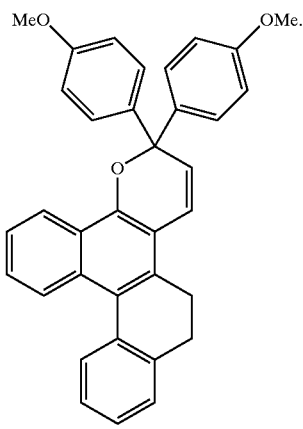

9. Compounds according to claim 1, characterised in that they have the following formula:

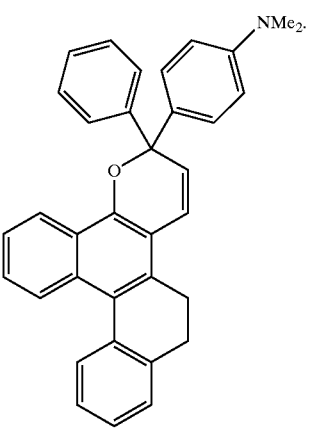

10. Compounds according to claim 1, characterised in that they have the following formula:

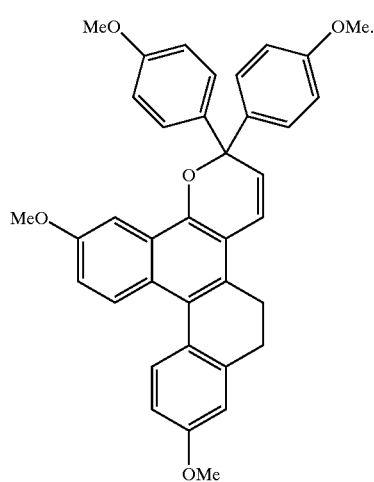

11. Compounds according to claim 1, characterised in that they have the following formula:

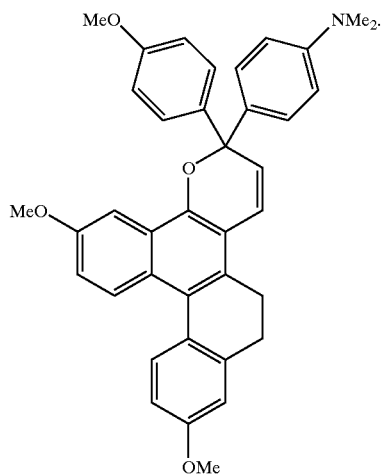

12. Compounds according to claim 1, characterised in that they have the following formula:

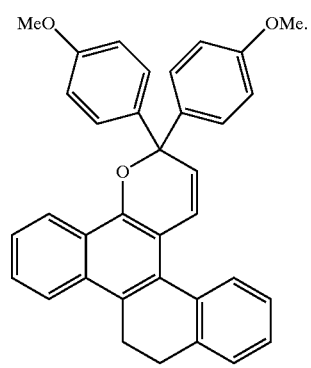

13. Compounds according to claim 1, characterized in that they have the following formula:

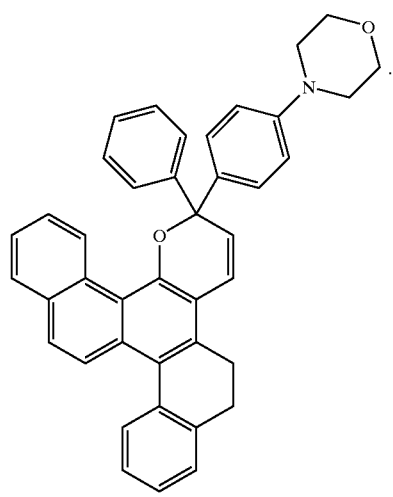

14. Compounds according to claim 1, characterized in that they have the following formula: